(12) United States Patent
Smith et al.

(10) Patent No.: US 12,245,786 B2
(45) Date of Patent: Mar. 11, 2025

(54) JAW APPARATUS AND TECHNIQUES TO MAINTAIN ENGAGEMENT UPON TISSUE SEPARATION

(71) Applicant: OLYMPUS CORPORATION, Tokyo (JP)

(72) Inventors: Adam Lee Smith, Palm Desert, CA (US); David A. Desmarais, Seattle, WA (US)

(73) Assignee: Olympus Corporation, Tokyo (JP)

( * ) Notice: Subject to any disclaimer, the term of this patent is extended or adjusted under 35 U.S.C. 154(b) by 323 days.

(21) Appl. No.: 17/808,682

(22) Filed: Jun. 24, 2022

(65) Prior Publication Data

US 2022/0409225 A1 Dec. 29, 2022

Related U.S. Application Data

(60) Provisional application No. 63/214,577, filed on Jun. 24, 2021.

(51) Int. Cl.
*A61B 17/28* (2006.01)
*A61B 17/29* (2006.01)

(52) U.S. Cl.
CPC .... *A61B 17/282* (2013.01); *A61B 2017/2929* (2013.01)

(58) Field of Classification Search
CPC ............... A61B 17/282; A61B 17/32; A61B 2017/2929; A61B 2017/2936; A61B 2017/2944; A61B 2017/320044
See application file for complete search history.

(56) References Cited

U.S. PATENT DOCUMENTS 4,819,938 A * 4/1989 Hill ...................... A63B 47/02
473/133
4,887,612 A * 12/1989 Esser ..................... A61B 10/06
606/174

(Continued)

FOREIGN PATENT DOCUMENTS

JP H10192290 7/1998

OTHER PUBLICATIONS

"International Application Serial No. PCT JP2022 026437, International Search Report mailed Sep. 20, 2022", 4 pgs.

(Continued)

*Primary Examiner* — Tan-Uyen T Ho
*Assistant Examiner* — Cherie M Poland
(74) *Attorney, Agent, or Firm* — Schwegman Lundberg & Woessner, P.A.

(57) ABSTRACT

Disclosed embodiments include apparatuses for and methods of separating tissue with opposing jaw members having distal ends that translate toward a surface of the tissue as the jaw members are rotated outwardly to maintain engagement with the tissue. In an illustrative embodiment, an apparatus includes jaw members rotatably coupled adjacent to their proximal ends. The jaw members define opposing outwardly-facing curved channels disposed between their proximal and distal ends that slidably engage a distal pin. A bracket defines a distal socket that receives the distal pin. As the jaw members are motivated in a distal direction relative to the bracket toward the distal pin, engagement of the distal pin with the outwardly-facing curved channels causes the jaw members to rotate to cause the distal ends of the jaw members move outwardly transversely to the distal direction while the distal ends translate in the distal direction.

18 Claims, 9 Drawing Sheets

(56) References Cited

U.S. PATENT DOCUMENTS

| | | |
|---|---|---|
| 5,431,674 A | 7/1995 | Basile et al. |
| 6,019,780 A | 2/2000 | Lombardo et al. |
| 8,663,270 B2 | 3/2014 | Donnigan et al. |
| 2013/0253540 A1 | 9/2013 | Castro et al. |
| 2018/0153629 A1 | 6/2018 | Wallace |
| 2019/0254644 A1 | 8/2019 | Mishra et al. |

OTHER PUBLICATIONS

"International Application Serial No. PCT JP2022 026437, Written Opinion mailed Sep. 20, 2022", 6 pgs.

* cited by examiner

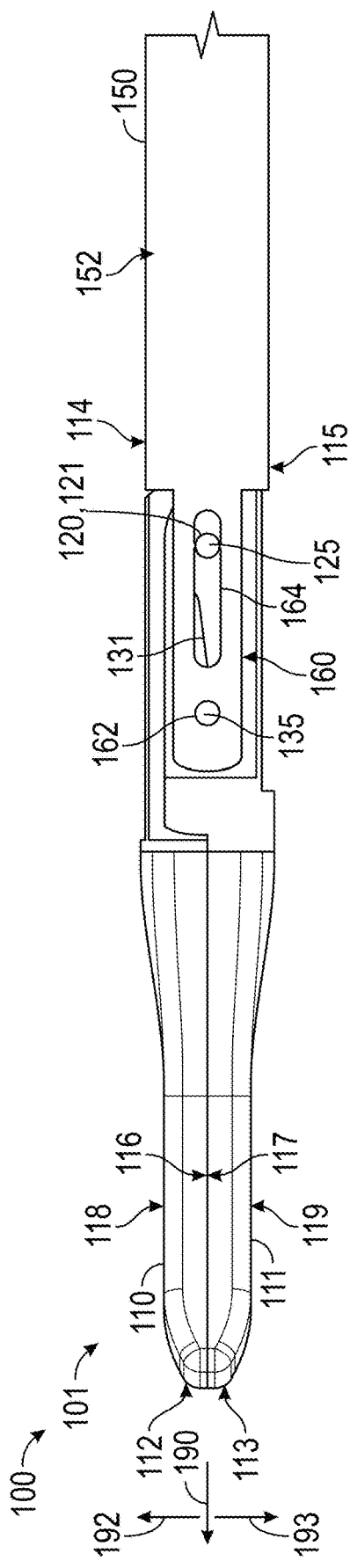
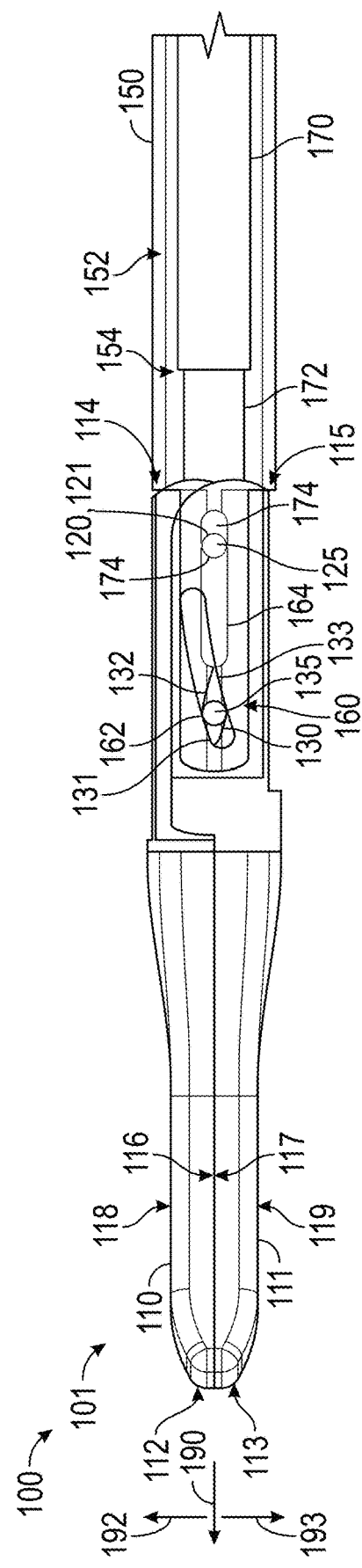
FIG. 1A
FIG. 1B

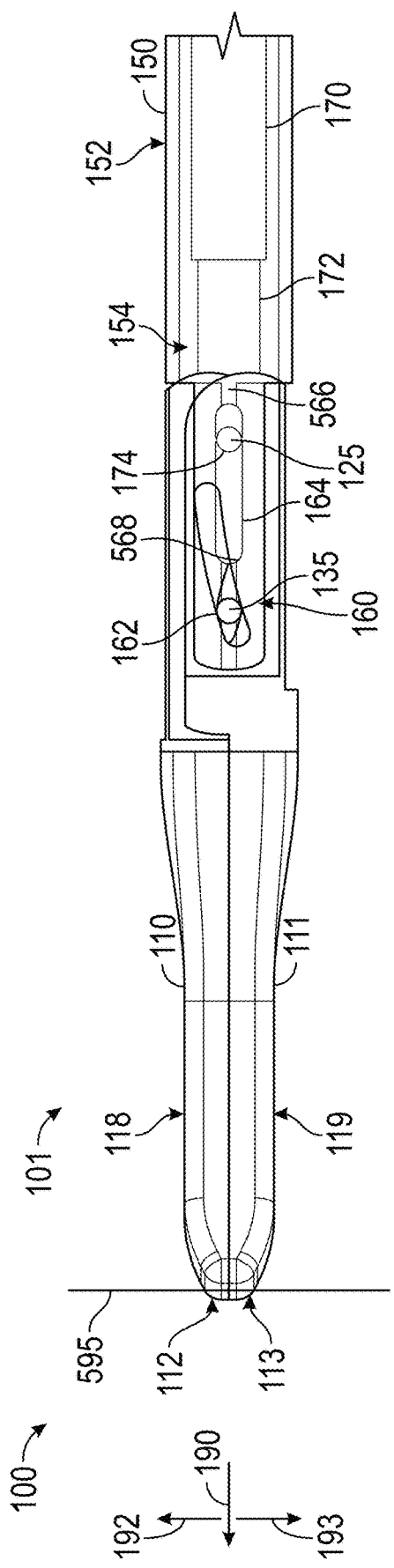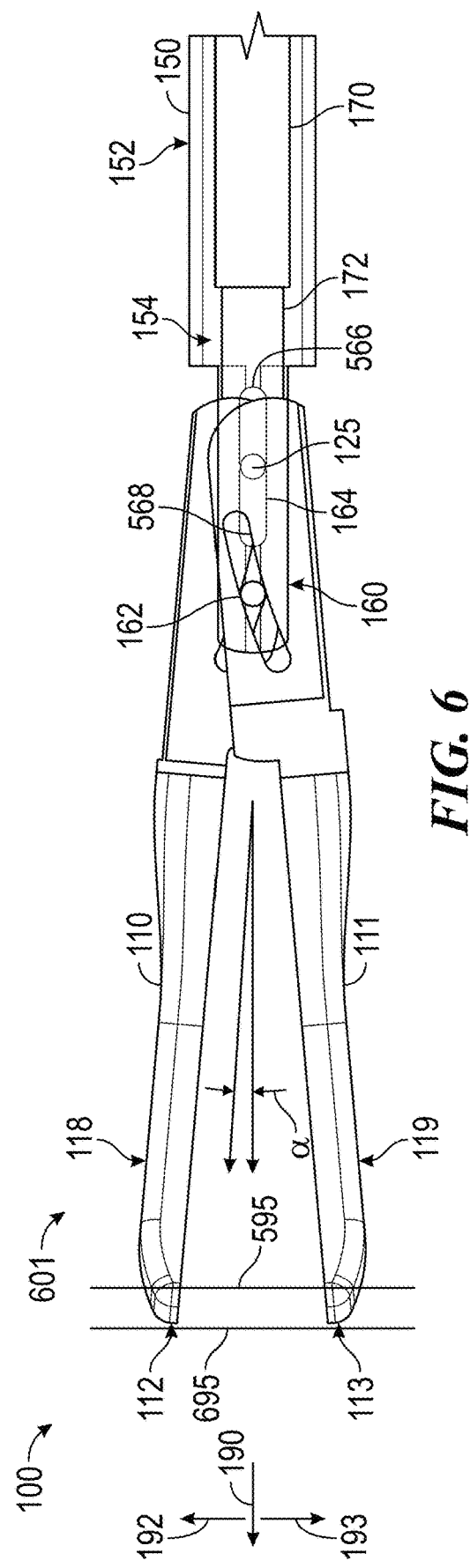

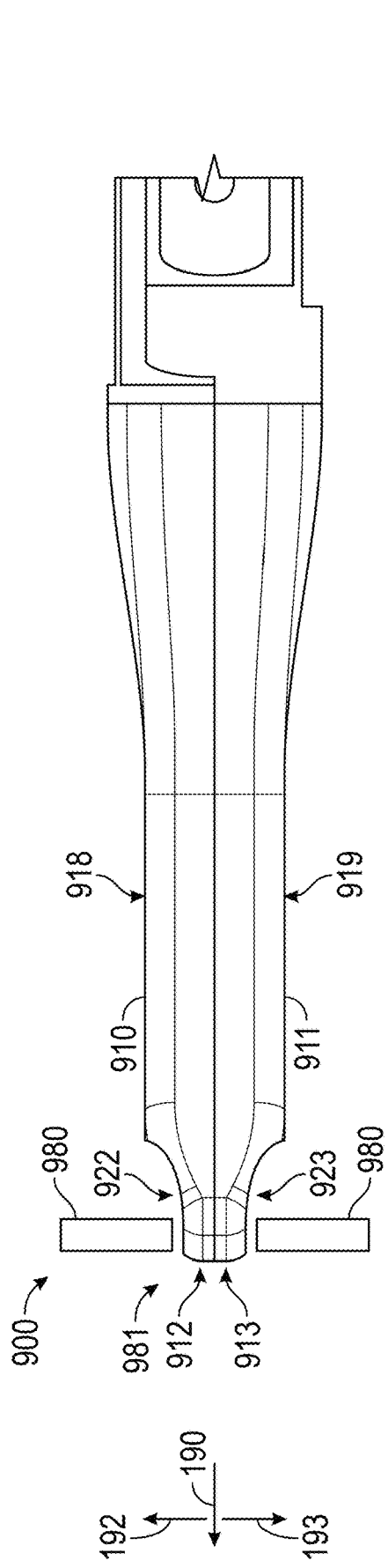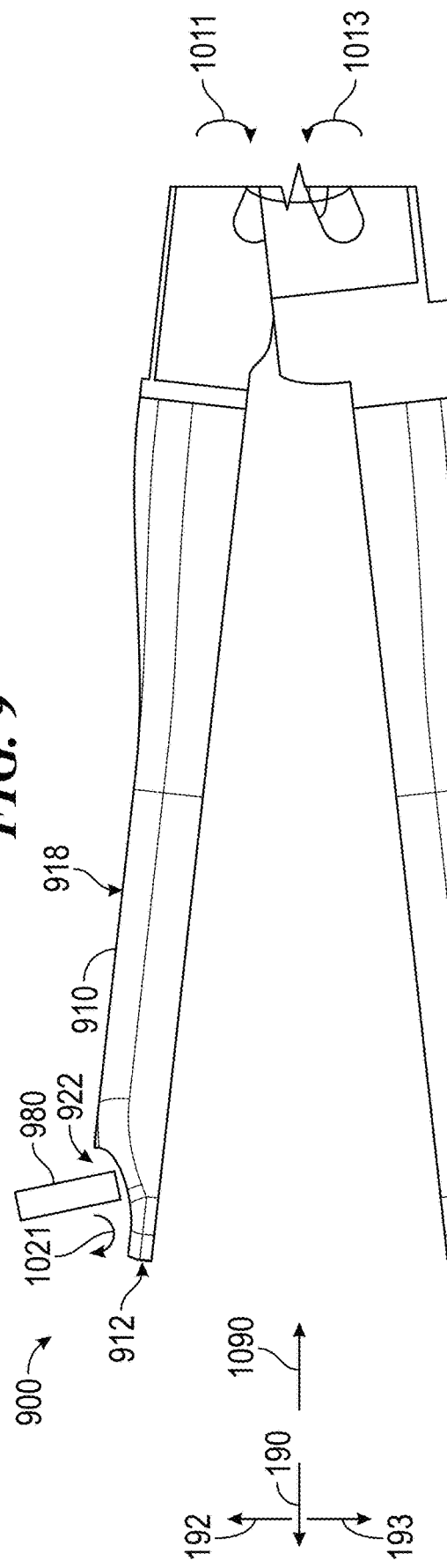

JAW APPARATUS AND TECHNIQUES TO MAINTAIN ENGAGEMENT UPON TISSUE SEPARATION

PRIORITY CLAIM

This application claims the benefit of priority to U.S. Provisional Patent Application Ser. No. 63/214,577, filed Jun. 24, 2021, the contents of which are hereby incorporated by reference in their entirety.

INTRODUCTION

Medical personnel sometimes employ blunt dissection to displace one or more tissue layers to access a structure beneath the tissue layers. One way to bluntly dissect the tissue is to insert a tool with opposably-hinged jaws into an incision or opening in the tissue surface and then open the jaws to spread apart the tissue layers. In a conventional hinged tool, the jaws rotate about a fulcrum. Thus, as a matter of geometry, as the jaws rotate outwardly to separate the tissue layers, the ends of the jaws also will rotate rearwardly—away from the tissue layers. The rearward motion of the jaws thus tends to withdraw the jaws from the tissue layers even as the jaws are opened in an attempt to separate the tissue layers, which may result in the tissue layers slipping from the jaws. In an effort to prevent the jaws from fully withdrawing from the tissue layers such that the tissue slips off of the distal end of the jaws, medical personnel sometimes manually thrust the conventional hinged tool forward. Unfortunately, it is difficult to precisely control the amount of forward movement induced at the distal tip during this type of coarse manual movement.

SUMMARY

Disclosed embodiments include apparatuses for and methods of separating tissue with opposing jaw members in which distal ends of the jaw members translate distally toward a surface of the tissue as the jaw members are rotated outwardly to maintain engagement with the tissue.

In an illustrative embodiment, an apparatus includes jaw members rotatably coupled adjacent to a proximal end of each of the jaw members by a proximal pin. The jaw members define opposing outwardly-facing curved channels disposed between the proximal end and a distal end of each of the jaw members. The opposing outwardly-facing curved channels slidably engage a distal pin. A bracket defines a distal socket that receives the distal pin. Motivating the proximal pin toward the distal pin causes the distal pin to engage the outwardly-facing curved channels to cause the distal ends of the jaw members to translate in a distal direction while the distal ends move outwardly transversely to the distal direction.

In another illustrative embodiment, an apparatus includes a proximal pin, a distal pin, and two jaw members. Each of the jaw members includes an outer surface that extends from a proximal end to a distal end and each of the jaw members defines a proximal socket configured to engage the proximal pin. Each of the jaw members also defines a curved channel disposed between the proximal socket and the distal end and having a concave side that faces the outer surface, where the curved channel is configured to slidably engage the distal pin to cause outward rotation of the jaw member around the proximal pin. A bracket defines a distal socket configured to engage the distal pin and a proximal channel having a proximal edge and a distal edge and configured to slidably engage the proximal pin. Motivating the proximal pin toward the distal edge of the proximal channel causes the distal ends of the jaw members to move outwardly transversely to the distal direction while the distal ends translate in the distal direction.

In another illustrative embodiment, a method includes inserting distal ends of two opposing jaw members movably received in a bracket into an opening in a tissue surface and opposing outer surfaces of the jaw members engage portions of the tissue surface on opposing sides of the opening. The opposing jaw members are rotatably coupled toward a proximal end of the jaw members and slidably engaged by a distal pin at opposing outwardly-facing curved channels disposed between the proximal end and a distal end of each of the jaw members. A force is applied in to the proximal end of the two opposing jaw members in a distal direction to cause the distal ends to translate relative to the bracket in the distal direction to maintain contact with the tissue surface while engagement of the distal pin with the opposing outwardly-facing curved channels imparts outward rotation to the jaw members to separate the opposing sides of the opening in the tissue surface.

In addition to the above described benefits of the jaws moving forward while opening, under various circumstances additional benefits may be realized by the jaws moving backwards (in the proximal direction) while the jaws are closing. For example, the rearward jaw motion may pull tissues being grasped slightly rearward for increased separation from adjacent tissues that are not being grasped.

Further features, advantages, and areas of applicability will become apparent from the description provided herein. It will be appreciated that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings:

FIG. 1A is a side view of an apparatus with translating jaw members for separating tissue;

FIGS. 1B, 5, 6, and 7 are side views in partial cutaway of the apparatus of FIG. 1A;

FIGS. 9 and 10 are side views of another embodiment of the apparatus of FIG. 1A.

DETAILED DESCRIPTION

Figure 2:
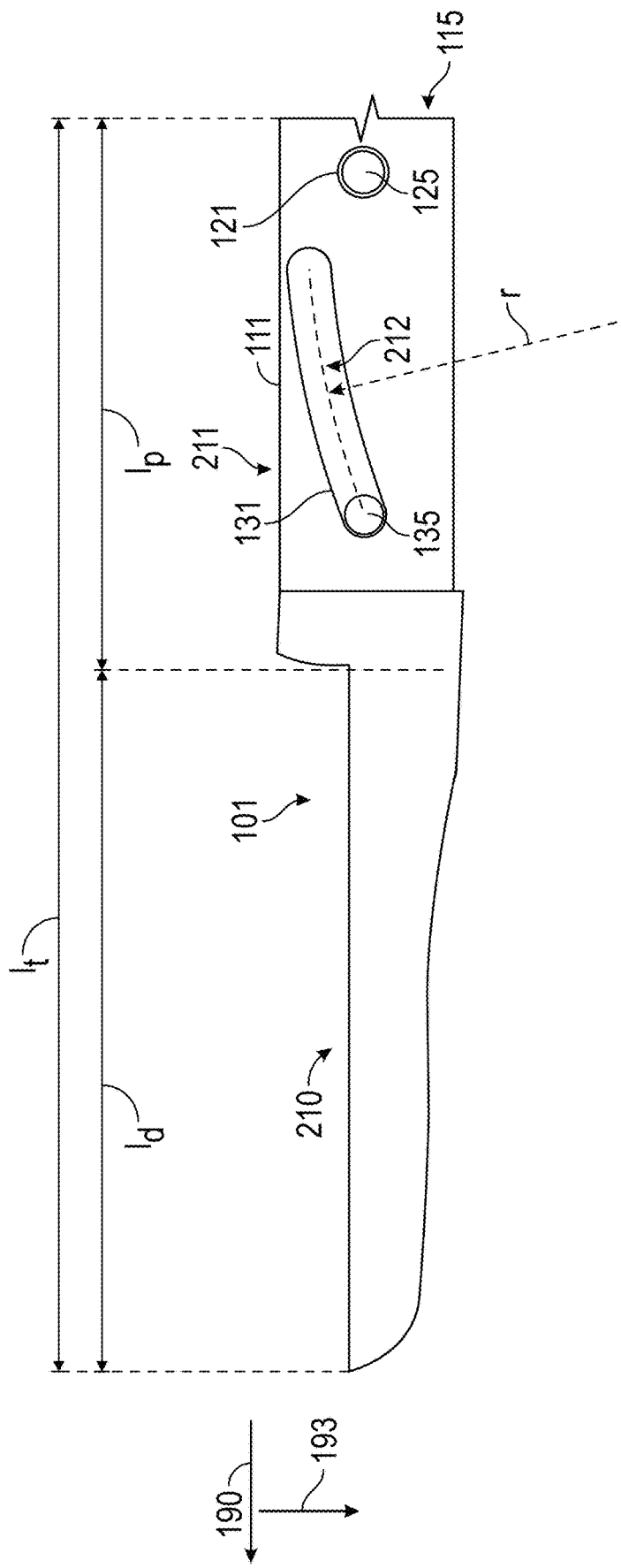
FIGS. 2-4 are side views of a jaw member of the apparatus of FIG. 1A.

The following description explains, by way of illustration only and not of limitation, various embodiments.

By way of a non-limiting introduction and overview, in various embodiments, an apparatus includes jaw members rotatably coupled adjacent to a proximal end of each of the jaw members by a proximal pin. The jaw members define opposing outwardly-facing curved channels disposed between the proximal end and a distal end of each of the jaw members. The opposing outwardly-facing curved channels slidably engage a distal pin. A bracket defines a distal socket that receives the distal pin. Motivating the proximal pin in a distal direction relative to the bracket toward the distal pin causes the distal pin to engage the outwardly-facing curved channels to cause the distal ends of the jaw members to translate in a distal direction while the distal ends move outwardly transverse to the distal direction. When the distal ends of the jaw members are placed against sides of an opening in a tissue surface to be separated, the translation of the distal ends of the jaw members as the jaw members are rotated helps to maintain contact of the distal ends with the sides of the opening to separate the tissue.

Now that a general overview has been given, details of various embodiments will be explained by way of non-limiting examples given by way of illustration only and not of limitation.

Referring to FIGS. 1A and 1B, an illustrative apparatus 100 includes two opposable jaw members 110 and 111. In various embodiments, the jaw members 110 and 111 each have a distal end 112 and 113 and a proximal end 114 and 115, respectively. The jaw members 110 and 111 each have an inner surface 116 and 117 and an outer surface 118 and 119, respectively. In various embodiments, the jaw members 110 and 111 meet along the inner surfaces 116 and 117, respectively, when the apparatus 100 is in a closed, starting position 101 as shown in FIGS. 1A and 1B. In various embodiments, the outer surfaces 118 and 119 may taper between the proximal ends 114 and 115 and the distal ends 112 and 113, respectively to facilitate insertion of the jaw members 110 and 111 of the apparatus 100 into a confined space.

In various embodiments, the jaw members 110 and 111 are rotatably coupled. The jaw members 110 and 111 each define a proximal socket 120 and 121 toward proximal ends 114 and 115 of the jaw members 110 and 111, respectively. At least one of the proximal sockets 120 and 121 is configured to rotatably receive a proximal pin 125, enabling the jaw members 110 and 111 to rotate relative to each other about the proximal pin 125. In various embodiments, the jaw members 110 and 111 each also define a curved channel 130 and 131 that is disposed between the proximal sockets 120 and 121 and the distal ends 112 and 113 of the jaw members 110 and 111, respectively. The curved channels 130 and 131 are outward-facing, with a concave side 132 of the curved channel 130 facing the outer surface 116 of the jaw member 110 and a concave side 133 of the curved channel 131 facing the outer surface 117 of the jaw member 111. Operation of the curved channels 130 and 131 in directing the motion of the jaw members 110 and 111 is further described below.

In various embodiments, the apparatus 100 includes a base 150 that movably supports the jaw members 110 and 111. The base 150 includes a handle 152 that enables a user of the apparatus 100 to grip, position, or otherwise support the apparatus 100. The base 150 also includes a bracket 160 that is movably coupled with the jaw members 110 and 111. In various embodiments, the bracket 160 defines a distal socket 162 that is configured to receive a distal pin 135 that engages the curved channels 130 and 131 of the jaw members 110 and 111, respectively, as further described below. The bracket 160 also defines a proximal channel 164 between the distal socket 162 and the handle 152 that slidably receives the proximal pin 125 extending from the jaw members 110 and 111.

In various embodiments, the apparatus 100 also includes a shaft 170 that is slidably received within a lumen 154 defined by the base 150 and extending through the handle 152 and the bracket 160. In various embodiments, the shaft 170 includes a coupling 172 that defines a shaft socket 174 to engage the proximal pin 125. In various embodiments, the shaft 170 is used to motivate the proximal pin 125 and, thus, motivate the jaw members 110 and 111 in a distal direction 190 to cause the jaw members 110 and 111 to translate in the distal direction 190. As the jaw members 110 and 111 translate in the distal direction 190, engagement of the curved channels 130 and 131 with the distal pin 135 causes the jaw members 110 and 111 to rotate in opposite directions about the proximal pin 125. The opposite rotation of the jaw members 110 and 111 about the proximal pin 125 causes the distal tips 112 and 113 to spread apart in directions 192 and 193, respectively, outwardly and transversely to the distal direction 190 as further described below.

As previously stated, the translation of the proximal pin 125 in the distal direction 190 causes the distal ends 112 and 113 of the jaw members 110 and 111 to advance in the distal direction 190. At the same time, the sliding engagement of the distal pin 135 with each of the curved channels 130 and 131 of the jaw members 110 and 111, respectively, allows for the translation of the jaw members 110 and 111 to advance the distal ends 112 and 113 in the distal direction 190 while also causing the distal ends 112 and 113 to spread apart.

Figure 3:
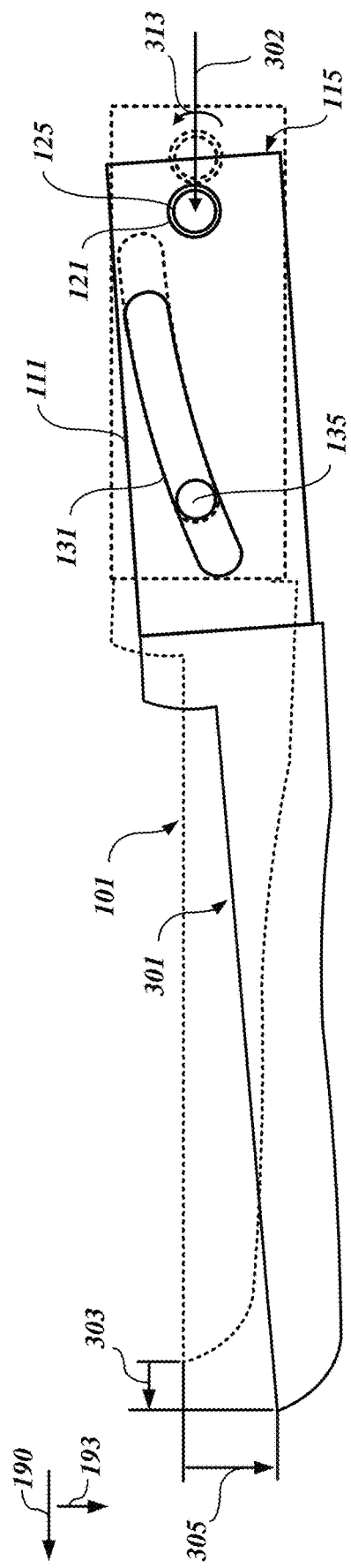
Figure 4:
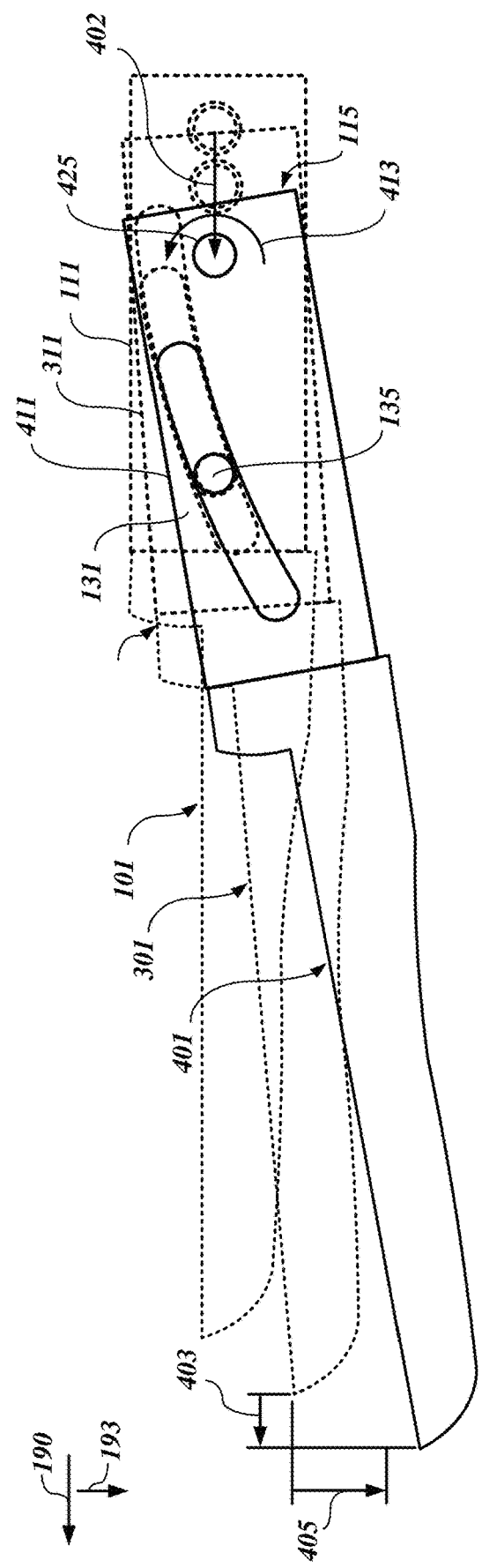

To illustrate operation of the apparatus 100, FIGS. 2-4 show movement of the jaw member 111 as a result of forces applied to the proximal pin 125 and engagement of the curved channel 131 of the jaw member 111 with the distal pin 135. To illustrate movement of the jaw member 111 in FIGS. 2, 3, and 4, previous positions of the jaw member 111 are represented by dotted lines in FIGS. 3 and 4. Movement of both jaw members 110 and 111 is described below with reference to FIGS. 5-7. It will be appreciated that, although specific examples of positions of the apparatus are shown and described with reference to FIGS. 3-7, the positions are for illustration and the apparatus 100 may be manipulated through a continuous range of positions to and through the positions specifically illustrated and described herein.

Referring to FIG. 2, the jaw member 111 is in the closed, starting position 101. (The starting position 101 is also shown in FIGS. 1A and 1B with the distal ends 112 and 113 of the jaw members 110 and 111 positioned together.) The jaw member 111 defines the proximal socket 121 that receives the proximal pin 125 and the curved channel 131 that slidably receives the distal pin 135, as previously described with reference to FIGS. 1A and 1B. In various embodiments, the curved channel 131 includes a radial curve having a radius r. For example, when the total length $l_t$ of the jaw member 111 is approximately 37.24 millimeters (mm), with a distal length $l_d$ of a jaw section 210 of approximately 22.5 mm and a proximal length $l_p$ of a hinge section 211 rearward of the jaw section 210 of approximately 14.74 mm, the radius r may be 20 mm with a center of curvature located proximal from a midpoint 212 of the curved channel 131. Thus, in various embodiments, the radius r is approximately 53.7% of the total length lt of the jaw member $l_t$. In some embodiments, the radius r is within the range of 50% to 58% of the total length of the jaw member 111. For example, in the example of FIG. 2, the radius r is 53.7% of the total length $l_t$ of the jaw member 111.

However, embodiments are not limited to any particular dimensions. For example, it will be appreciated that a smaller radius r will result in a more sharply curved channel 131. The smaller radius r thus will result in more rotation of the jaw member 111 per unit of translation of the jaw member 111 and, thus, a more rapid opening of the jaw member 111 as the jaw member 111 translates in the distal direction 190. By contrast, a larger radius r will result in a less sharply curved channel 131. The larger radius r will result in less rotation of the jaw member 111 per unit of translation of the jaw member 111 and, thus, a more gradual opening of the jaw member 111 as the jaw member 111 translates in the distal direction 190.

Referring to FIG. 3, application of a force 302 to the proximal pin 125 in the distal direction 190 (such as may be exerted by the shaft 170 as described with reference to FIGS. 1A and 1B) results in translation and rotation of the jaw member 111 to a first open position 301. In various embodiments, engagement of the proximal pin 125 with the proximal socket 121 conveys the force 302 to the jaw member 111. In response to application of the force 302, the jaw member 331 translates a distance 303 in the proximal direction 190. In various embodiments, the proximal pin 125 is constrained to slide within the proximal channel 164 of the bracket 160 (FIGS. 1A and 1B), thus causing the proximal pin 125 to move in the distal direction 190.

With the translation of the jaw member 111, the curved channel 131 of the jaw member 111 engages the distal pin 135. In various embodiments, the distal pin 135 is received in the distal socket 162 of the bracket 160 (FIG. 1A) which remains stationary as the jaw member 111 is moved. The shape of the curved channel 131 permits the translation of the jaw member 111 while, at the same time, the engagement of the curved channel 131 with the distal pin 135 causes a rotation 313 of the jaw member 111. The rotation 313 causes the distal end 113 of the jaw member 111 to translate a distance 305 in the transverse direction 193.

As a result, if the distal end 113 is applied to a tissue layer, the distal end 113 of the jaw member 111 moves the tissue through the distance 305 in the transverse direction 193. At the same time, translation of the distal end 113 through the distance 303 in the distal direction 190 helps to keep the distal end 113 in contact with the tissue surface as the jaw member 111 is rotated.

Referring to FIG. 4, application of a continued force 402 to the proximal pin 125 in the distal direction 190 results in further translation and rotation of the jaw member 111 to a second open position 401. In response to application of the continued force 402, the jaw member 111 translates a distance 403 in the distal direction 190. With the translation of the jaw member 111, the curved channel 131 of the jaw member 111 engages the distal pin 135 to impart a further rotation 413 to the jaw member 111. As a result of the rotation, the distal end 113 of the jaw member 111 translates a distance 405 in the transverse direction 193. Again, if the distal end 113 is applied to a tissue layer, the distal end 113 of the jaw member 111 moves the tissue through the distance 405 in the transverse direction 193. At the same time, translation of the distal end 113 through the distance 403 in the distal direction 190 helps to maintain contact between the distal end 113 as the jaw member 111 is rotated.

Although not shown in FIGS. 2-4, it will be appreciated that engagement of the curved channel 130 of the jaw member 110 with the distal pin 135 (FIGS. 1A and 1B) results in analogous movement of the jaw member 130 with opposite rotation of the jaw member 110 as compared to that of the jaw member 111

Figure 7:
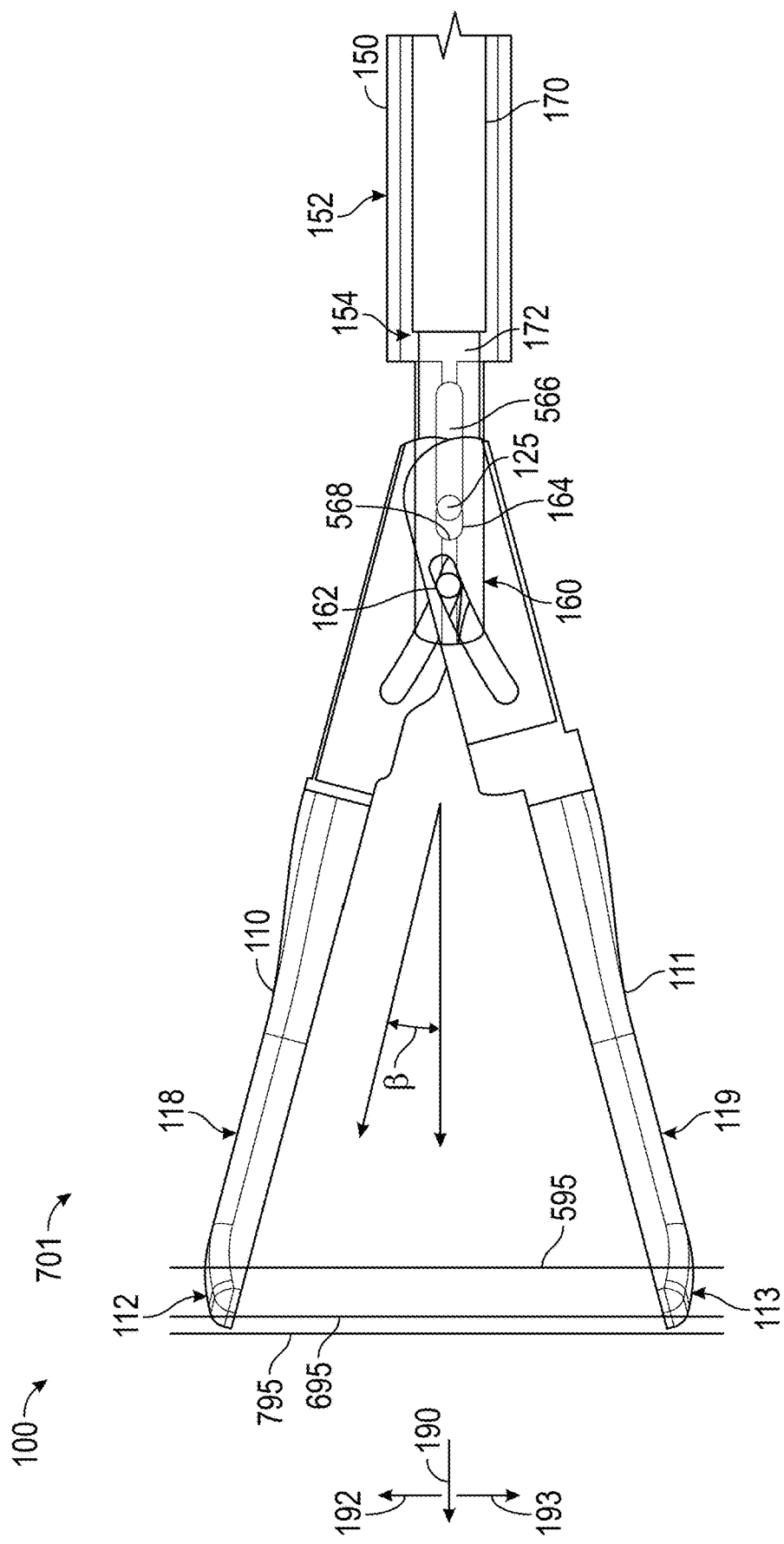

Referring additionally to FIGS. 5-7, the apparatus 100 is operated to open the jaw members 110 and 111 to displace tissue layers. With particular reference to FIG. 5, the apparatus 100 is in the closed starting position 101 with distal ends 112 and 113 positioned against a first reference plane 595. In use, the distal ends 112 and 113 may be inserted into an opening or other incision made in a one or more tissue layers (not shown). The first reference plane 595 thus represents a position of the distal ends 112 and 113 at an initial insertion depth within the tissue. The base 150 may be used to position the apparatus 100 at the desired location. The handle 152 may be engaged by an operator to place and secure the apparatus 100 at the desired location as the jaw members 110 and 111 are opened, such as that shown in FIGS. 5-7.

In various embodiments, to open the jaw members 110 and 111 to displace the tissue, a force is applied the shaft 170. As also previously described, the proximal pin 125 is slidably received within the proximal channel 164 defined by the bracket 160. The proximal pin 125 is slidable between a proximal edge 566 and a distal edge 568 of the proximal channel 164 in response to movement of the shaft 170, as further described below. As also previously described, in various embodiments, the shaft 170 includes the coupling 172 that defines the shaft socket 174 that receivably engages the proximal pin 125. As a result of the engagement of the shaft socket 174 with the proximal pin 125, movement of the shaft 170 moves the proximal pin 125 to motivate the jaw members 110 and 111.

With particular reference to FIG. 6, a force is applied to the shaft 170 to advance the shaft 170 in the distal direction 190, manipulating the apparatus 100 into a first open position 601. The advancement of the shaft 170 advances the proximal pin 125 away from the proximal edge 566 of the proximal channel 164 toward the distal edge 568 of the proximal channel 164. Advancing the proximal pin 125, as previously described with specific reference to the jaw member 111, causes the jaw members 110 and 111 to translate in the distal direction 190. As also described with reference to FIGS. 2-4, the translation of the jaw members 110 and 111 results in the curved channels 130 and 131 of the jaw members 110 and 111, respectively, engaging the distal pin 135 received in the distal socket 162 of the bracket 160. As also previously described, the shape of the curved channels 130 and 131 permits translation of the jaw members 110 and 111 past the distal pin 135. At the same time, engagement of the curved channels 130 and 131 with the distal pin 135 causes the jaw members 110 and 111 to rotate in opposite directions to move the jaw members 110 and 111 into an open position to displace tissue layers.

Thus, in the first open position 601, the resulting rotation of the jaw members 110 and 111 results in an outward rotation of each of the jaw members 110 and 111 by an angle α. The outward rotation causes each of the distal ends 112 and 113 of the jaw members 110 and 111 to translate in opposite directions 192 and 193, respectively, transverse to the distal direction 190. In the first open position 601, as the distal ends 111 and 113 of the jaw members 110 and 111 open, without moving the base 150, the distal ends 111 and 113 also translate from a first reference plane 595 to a second reference plane 695. The translation to the second reference plan 695 helps to maintain engagement of the distal tips 112 and 113 with the tissue as the jaw members 110 and 111 move outwardly to separate the tissue.

With particular reference to FIG. 7, additional force is applied to the shaft 170 to further advance the shaft 170 in the distal direction 190, thereby manipulating the apparatus 100 into a second open position 701. The further advancement of the shaft 170 advances the proximal pin 125 further away from the proximal edge 566 of the proximal channel 164 toward the distal edge 568 of the proximal channel 164, causing the jaw members 111 and 113 to further translate in the distal direction 190. Engagement of the curved channels 130 and 131 of the jaw members 110 and 111 also induces further outward rotation of each of the jaw members 110 and 111 by an angle β. The outward rotation causes each of the distal ends 112 and 113 of the jaw members 110 and 111 to translate in opposite directions 192 and 193, respectively, transverse to the distal direction 190. As with the movement to the first open position 601, without moving the base 150, the distal ends 111 and 113 translate from the second reference plane 695 to a third reference plane 795 to maintain engagement of the distal tips 112 and 113 with the tissue as the jaw members 110 and 111 move outwardly to separate the tissue.

Figure 8:
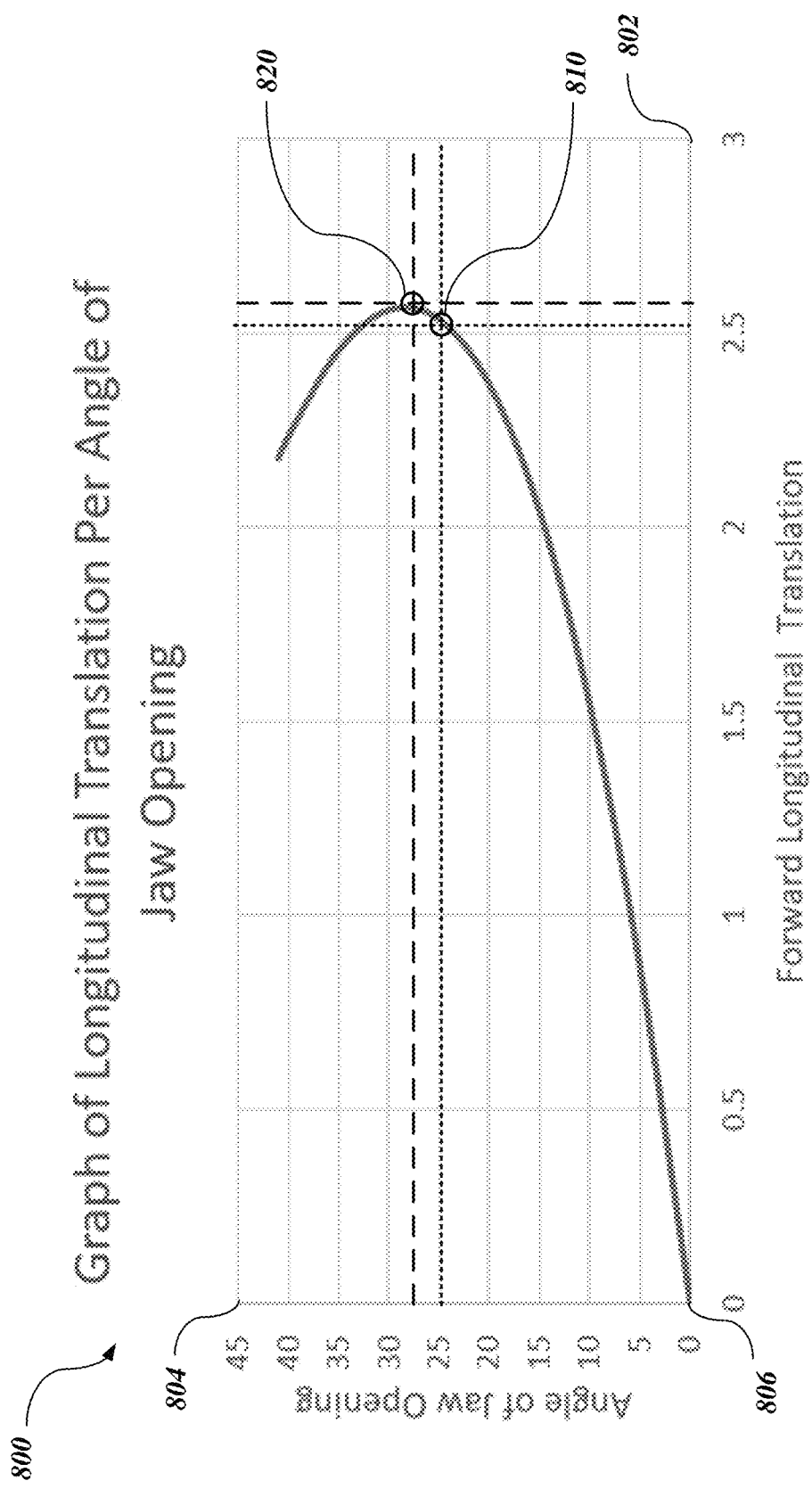
FIG. 8 is a graph depicting relative distal movement of the distal ends of the apparatus of FIG. 1A relative to a jaw opening angle.

Referring additionally to FIG. 8, according to various embodiments, a graph 800 plots a forward longitudinal translation 802 of the jaw members 110 and 111 relative to angle of jaw opening 804. The graph 800 represents the relative motion in the distal direction 190 of the jaw members 110 and 111, such as that shown in the translation from the first reference plane 595 to the second and third reference planes 695 and 795, respectively, relative to an angle of jaw opening 804 increasing from zero to the outward rotation angles α and β, of FIGS. 5-7. It will be appreciated that the translation of the jaw members 110 and 111 relative to the angle of jaw opening is based on dimensions of the jaw members 110 and 111, a shape and radius 201 (FIG. 2) of the curved channels 130 and 131, and other parameters, as previously described with reference to FIG. 2.

In a particular embodiment, at a first point 810 representing an angle of approximately 25 degrees of outward rotation of jaw opening, the forward longitudinal translation in the distal direction 190 is in excess of 2.5 mm. At a second point 820 representing an angle of approximately 27.5 of outward rotation of jaw opening, the forward longitudinal translation in the distal direction 190 reaches nearly 2.6 mm. It will be appreciated that, after the second point 820, in a particular embodiment, no additional forward longitudinal translation of the jaw members 110 and 111 results from additional opening of the jaw members. Further movement of the proximal pin 125 may cause portions of the jaw members 110 and 111 to continue to translate beyond this point. However, as the jaw members 110 and 111 continue to open, the continued opening of the jaw members 110 and 111 may result in the distal ends 112 and 113 rotating rearwardly by a distance that exceeds the forward distal translation of the jaw members 111 and 113.

As previously mentioned, the translation of the jaw members 110 and 111 also occurs when the jaw members 110 and 111 are closed in order to retract tissue held between the jaw members 110 and 111. Thus, for example, the rearward, proximal motion of the jaw members 110 and 111 pull tissues being grasped slightly rearward for increased separation from adjacent tissues that are not being grasped.

Referring additionally to FIG. 9, in various embodiments, jaw members 910 and 911 may include distal ends 912 and 913 that include outwardly-facing concave end surfaces 922 and 923. The concave end surfaces 922 and 923 may promote continued engagement of the distal ends 912 and 913 with one or more tissue layers 980 as the jaw members 910 and 911 are rotated to separate the tissue layers. As previously described, the distal ends 912 and 913 may be inserted into an opening 981, such as an incision, in the tissue layers 980 and the apparatus 900 is operated as described with reference to FIGS. 1A-7 to separate the tissue layers 980 around the opening 981.

Referring additionally to FIG. 10, as the jaw members 910 and 911 are oppositely rotated in the directions 1011 and 1013 as the jaw members 910 and 911 are opened, the concave end surfaces 922 and 923 also rotate in directions 922 and 923. The concave end surfaces 922 and 923 thus assume an attitude that may apply some force to the tissue layers 980 in a rearward direction 1090 opposite to the distal direction 190. As a result, as the distal ends 912 and 913 further translate into and/or toward the tissue layers 980, the force applied in the rearward direction 1090 against the tissue layers may help hold the distal ends 912 and 913 against the tissue layers as the distal ends 912 and 913 further advance in the distal direction 190.

Figure 11:
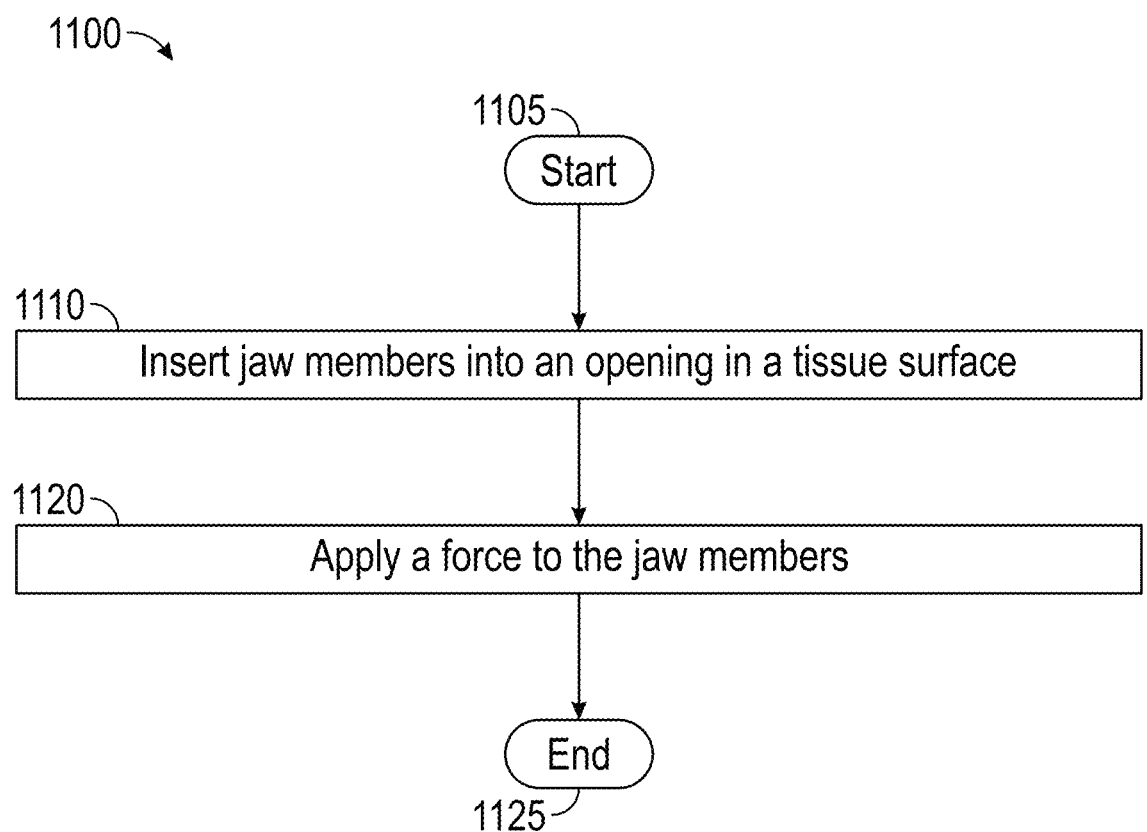
FIG. 11 is a flow diagram of an illustrative method for j aw members to translate toward a tissue surface while jaw members move outwardly to separate the tissue.

Referring additionally to FIG. 11, an illustrative method 1100 is provided for separating tissue with opposing jaw members having distal ends that translate toward a surface of the tissue as the jaw members are rotated outwardly to maintain engagement with the tissue. The method starts at a block 1105. At a block 1110, distal ends of two opposing jaw members movably received in a bracket are inserted into an opening in a tissue surface. Opposing outer surfaces of the jaw members engage portions of the tissue surface on opposing sides of the opening. The opposing jaw members are rotatably coupled toward a proximal end of the jaw members and are slidably engaged by a distal pin at opposing outwardly-facing curved channels disposed between the proximal end and a distal end of each of the jaw member. At a block 1120, a force is applied to the proximal end of the two opposing jaw members in a distal direction to cause the distal ends to translate in the distal direction relative to the bracket. Translation of the distal ends helps to maintain contact with the tissue surface while engagement of the distal pin with the opposing outwardly-facing curved channels imparts outward rotation to the jaw members to separate the opposing sides of the opening in the tissue surface. The method ends at the block 1125.

In some instances, one or more components may be referred to herein as "configured to," "configured by," "configurable to," "operable/operative to," "adapted/adaptable," "able to," "conformable/conformed to," etc. Those skilled in the art will recognize that such terms (for example "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While the disclosed subject matter has been described in terms of illustrative embodiments, it will be understood by those skilled in the art that various modifications can be made thereto without departing from the scope of the claimed subject matter as set forth in the claims.

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus comprising:
a pair of jaw members rotatably coupled adjacent to a proximal end of each jaw member of the pair of jaw members, wherein the pair of jaw members define opposing outwardly-facing curved channels disposed between the proximal end and a distal end of each jaw member of the pair of jaw members and the opposing outwardly-facing curved channels are configured to slidably engage a distal pin, and wherein each jaw member of the pair of jaw members includes an outwardly-facing concave end surface adjacent the distal end; and
a bracket that defines a distal socket that receives the distal pin,
wherein as the pair of jaw members are motivated in a distal direction relative to the bracket toward the distal pin, engagement of the distal pin with the outwardly-facing curved channels imparts outward rotation to the pair of jaw members to cause the distal ends of the pair of jaw members move outwardly transversely to the distal direction while the distal ends translate in the distal direction.

2. The apparatus of claim 1, wherein the bracket defines a proximal channel that slidably engages the proximal pin as the proximal pin is motivated toward the distal pin.

3. The apparatus of claim 2, further comprising a shaft configured to engage the proximal pin and to motivate the proximal pin to move within the proximal channel.

4. The apparatus of claim 1, wherein an outer surface of each jaw member of the pair of jaw members tapers inwardly toward the distal end.

5. The apparatus of claim 1, wherein motivating the proximal pin toward the distal pin causes the distal end of each jaw member of the pair of jaw members to translate in the distal direction during an initial twenty-five degrees of the outward rotation from a closed position of the pair of jaw members.

6. The apparatus of claim 1, wherein motivating the proximal pin toward the distal pin causes the distal end of each jaw member of the pair of jaw members to translate in the distal direction during an initial twenty-seven degrees of the outward rotation from a closed position.

7. The apparatus of claim 1, wherein a ratio of a radius of each the opposing outwardly-facing curved channels is one of: equal to 53.7% of a length of each jaw member of the pair of jaw members; within a range of 50% to 58% of a length of each jaw member of the pair of jaw members; or is within a range of 52% to 56% of a length of each jaw member of the pair of jaw members.

8. An apparatus comprising:
a proximal pin;
a distal pin;
two jaw members, wherein each jaw member of the two jaw members includes an outer surface that extends from a proximal end to a distal end, wherein the outer surface includes an outwardly-facing concave end surface adjacent the distal end, and each jaw member of the two jaw members defines:
a proximal socket configured to engage the proximal pin; and
a curved channel disposed between the proximal socket and the distal end and having a concave side that faces the outer surface, wherein the curved channel is configured to slidably engage the distal pin to cause outward rotation of each jaw member of the two jaw members around the proximal pin; and
a bracket that defines a distal socket configured to engage the distal pin and a proximal channel having a proximal edge and a distal edge and configured to slidably engage the proximal pin,
wherein motivating the proximal pin toward the distal edge of the proximal channel causes the distal ends of the jaw members to move outwardly transversely to a distal direction while the distal ends translate in the distal direction.

9. The apparatus of claim 8, further comprising a shaft configured to engage the proximal pin and to motivate the proximal pin to move within the proximal channel.

10. The apparatus of claim 9, wherein the bracket includes an interior channel configured to slidably receive the shaft therethrough.

11. The apparatus of claim 8, wherein the outer surface of each jaw member of the two jaw members tapers inwardly toward the distal end.

12. The apparatus of claim 8, wherein motivating the proximal pin toward the distal edge of the proximal channel causes the distal end of each jaw member of the two jaw members to translate in the distal direction during an initial twenty-five degrees of the outward rotation from a closed position of the two jaw members.

13. The apparatus of claim 8, wherein motivating the proximal pin toward the distal edge of the proximal channel causes the distal end of each jaw member of the two jaw members to translate in the distal direction during an initial twenty-seven degrees of the outward rotation from a closed position.

14. The apparatus of claim 8, wherein a ratio of a radius of the curved channel is one of equal to 53.7% of a length of each jaw member of the two jaw members; within a range of 50% to 58% of a length of each jaw member of the two jaw members; or is within a range of 52% to 56% of a length of each jaw member of the two jaw members.

15. A method comprising:
inserting distal ends of two opposing jaw members movably received in a bracket into an opening in a tissue surface, wherein opposing outwardly-facing concave end surfaces adjacent the distal ends of the two opposing jaw members engage portions of the tissue surface on opposing sides of the opening, wherein the two opposing jaw members are rotatably coupled toward a proximal end of the two opposing jaw members and slidably engaged by a distal pin at opposing outwardly-facing curved channels disposed between the proximal end and a distal end of each jaw member of the two opposing jaw members; and applying a force to the proximal end of the two opposing jaw members in a distal direction to cause the distal ends to translate relative to the bracket in the distal direction to maintain contact with the tissue surface while engagement of the distal pin with the opposing outwardly-facing curved channels imparts outward rotation to the two opposing jaw members to separate the opposing sides of the opening in the tissue surface.

16. The method of claim 15, further comprising holding the bracket in place relative to the opening in the tissue surface while applying the force in a distal direction to the proximal end of the two opposing jaw members to cause the distal ends to translate in the distal direction while the two opposing jaw members rotate outwardly the portions of the tissue surface.

17. The method of claim 15, further comprising using a shaft to apply the force in the distal direction to the proximal end of each of the two opposing jaw members.

18. The method of claim 15, wherein applying the force causes the distal end of each of the two jaw members to translate in the distal direction while each jaw member of the two opposing jaw members is outwardly rotating through a first twenty-five degrees of rotation.

* * * * *